United States Patent [19]

Hoffman et al.

[11] Patent Number: 5,198,535
[45] Date of Patent: Mar. 30, 1993

[54] PROTECTIVE MALARIA SPOROZOITE SURFACE PROTEIN IMMUNOGEN AND GENE

[75] Inventors: Stephen L. Hoffman, Gaithersburg; Yupin Charoenvit, Silver Spring, both of Md.; Richard Hedstrom, Cairo, Egypt; Srisin Khusmith; William O. Rogers, IV, both of Rockville, Md.

[73] Assignee: The United States of America as represented by the Secretary of the Navy, Washington, D.C.

[21] Appl. No.: 638,431

[22] Filed: Jan. 10, 1991

[51] Int. Cl.$^5$ .............................................. C07K 13/00
[52] U.S. Cl. .................................... 530/350; 530/300
[58] Field of Search ........................... 424/88; 530/350

[56] References Cited

FOREIGN PATENT DOCUMENTS

WO90/01496 2/1990 PCT Int'l Appl.

OTHER PUBLICATIONS

Khusmith et al, Science vol. 252:715–718 May 1991. "Protection against Malaria by Vaccination with Sporozoite surface protein 2 plus CS protein", not prior art, for information.

Walliker et al. Science vol. 236 Jun. 1987, Genetic Analysis of the Human Malaria Parasite *Plasmodium falciparum*.

Charoenvit et al. Inf. & Imm vol. 55 1987 pp. 604–608, Characterization of *Plasmodium yoelii*.

Monoclonal anlitsedes directed against stage-specific sporozoite antigens.

Hollingdale et al., Imm Letters vol. 25.

Non-CS pre-erythrocytic protection antigens Immunology Letter 25 1990.

Robson et al.; A Highly Conserved Amino-Acid Sequence . . . ; Sep. 1, 1988; Nature, vol. 335, p. 79.

*Primary Examiner*—Christine M. Nucker
*Assistant Examiner*—Hazel Sidberry
*Attorney, Agent, or Firm*—A. David Spevack; William C. Garvert

[57] ABSTRACT

A protein antigen (SSP2) on the surface of *Plasmodium sporozoites* is disclosed as a candidate immunogen for vaccination against malaria. This use of this protein, which is distinct from the extensively characterized circumsporozoite (CS) protein, will also facilitate research into host immunological responses to malaria. This antigen is detected by a monoclonal antibody (NYS4) which is specific for a 140 kilodalton (kD) protein on the sporozoite cell surface. Immunoreactive genomic clones are described which express this surface antigen gene and the primary nucleic acid sequence and the deduced amino acid sequence derived from this DNA sequence are disclosed. Unique repetitive sequences of amino acids are described which further demonstrate the distinction between SSP2 and the CS protein. A synthetic peptide containing repeating epitopes of SSP2 derived protein antigen and which are substantially shorter in length than the intact antigen are disclosed. The peptide when administered to a host elicits antibodies which bind to the SSP2 protein on the sporozoite surface. A recombinant plasmid bearing SSP2 DNA sequences expresses SSP2 epitopes in mammalian cells and the introduction of these transfected cells into mice elicits antibody and cytotoxic T-cell lymphocytic responses which confer partial protection to the recipient animals against challenge infection. In combination, the SSP2 protein and the CS protein elicit immunological responses in the mammalian host which confer 100% protection against challenge infection.

2 Claims, 1 Drawing Sheet

PROTECTIVE MALARIA SPOROZOITE SURFACE PROTEIN IMMUNOGEN AND GENE

BACKGROUND OF THE INVENTION

1. Field of the Invention

This invention relates to an immunologically active protein, and the gene which encodes it, useful in vaccination against malaria. More particularly, this invention relates to a protein antigen on the surface of *Plasmodium yoelii* sporozoites detected by a monoclonal antibody NYS4, clones of genomic and complementary DNA sequences specific for this and closely related proteins from malarial parasites which, when administered as vaccine components either alone or in combination with other malarial antigens, can confer protective immunity.

2. Description of the Prior Art

Prevention of infection by human malarias would alleviate a major health problem in the tropical and sub-tropical areas of the world. The most promising method for the control of malaria appears to be the development and use of vaccines.

Species of the genus Plasmodium are the etiological agents of malaria. These protozoan parasites have a complex life cycle involving reproduction in mammalian hosts and insect vectors. The infectious stage of the parasite is called the sporozoite. It is inoculated into a mammalian host by the bite of infected Anopheline mosquitos.

One approach to producing a malaria vaccine is to attempt to induce an immune response against the infective sporozoites themselves. This has been done by immunization of human and animal models with radiation attenuated sporozoites. These attenuated sporozoites consistently protect against challenge with infectious sporozoites (Nussenzweig et al., Nature 216:160, 1969, Clyde et al, Am. J. Med. Sci. 266:160, 1973, Rieckmann et al., Bull. W. H. O. 57, Suppl.1:261, 1979).

A surface protein of Plasmodium sporozoites, designated the circumsporozoite protein (CSP) has been identified and well characterized (Nussenzweig and Nussenzweig, Cell 42:401, 1985). The CSPs of several Plasmodium species have been described. They all contain tandem repeats of short peptide sequences as well as regions of non-repetitive sequence. While the existence of tandem repeats is a conserved feature of all CSP genes, the particular amino acid sequences which are repeated vary both between and within species. On the other hand, the non-repetitive sequences are well conserved both within and between species.

During the past decade, the primary strategy for malaria sporozoite vaccine development has been to produce vaccines that induce antibodies to the repeat region of the CSP. These antibodies are believed to prevent effective sporozoite invasion of hepatocytes (Mazier et al., Science 231:156, 1986, Young et al., Science 228:958,1985, Ballou et al., Science 228:996, 1985, Zavala, et al. Science 228: 1985, 1985). Thus far, protective immunity after immunization of humans (Ballou et al., Lancet 1:1277, 1987, Herrington et al, Nature 328:257, 1987) and non human primates with CSP based vaccines (Collins, et al. Am. J. Trop. Med. Hyg. 40:455, 1989) has been disappointing. Mice immunized with P. berghei subunit vaccines based on the CSP have been protected against moderate, but not against large challenge doses of sporozoites (Egan et al. Science 236:453, 1987, Zavala et al. J. Ex. Med. 166:1591, 1987, Hoffman et al., J. Immunol. 142: 3581, 1989, Romero et al. Eur. J. Immunol. 18: 1951, 1988). In the *P. yoelii* model system, mice have been immunized with a variety of synthetic peptides and recombinant proteins based on the CSP (Lal et al. Proc. Natl. Acad. Sci. USA 84:8647, 1987, Sedegah et al. in *Technological Advances in Vaccine Development* L. Lasky editor, New York, 1988, Sedegah et al., Bull. W. H. O., in press, Charoenvit et al., Bull. W. H. O., in press). In the majority of experiments, mice developed high levels of antibodies to the CSP, but were not consistently protected against challenge with *P. yoelii* sporozoites.

The failure of immunization with vaccines based on the CSP to provide the same solid immunity as immunization with radiation attenuated sporozoites suggests that although the CSP plays a role in immunity, there are other sporozoite antigens important in immunity to malaria. There is a need to identify, isolate and characterize these antigens so that they may be included in future malaria vaccines.

SUMMARY OF THE INVENTION

Accordingly, an object of this invention is a sporozoite surface antigen which is distinct from the CS protein. This antigen is designated Sporozoite Surface Protein 2 (SSP2). By SSP2 we refer both to the *P. yoelii* protein whose sequence is here disclosed and to the homologs of this protein which exist in other species of Plasmodium, including the human pathogens, *P. falciparum, P. vivax, P. ovale,* and *P. malariae*. These homologs may be recognized by their having both a predicted general structure similar to that of the *P. yoelii* SSP2 (FIG. 1), including a short hydrophobic leader sequence, a region containing perfect or degenerate tandem repeats of short peptide motifs, flanking regions containing non repetitive amino acid sequence, a membrane spanning domain and a cytoplasmic domain, and by their having an amino acid sequence which, at least in the non-repetitive regions of the sequence, bears substantial sequence similarity to the *P. yoelii* SSP2 amino acid sequence (Sequences 1 and 2).

Another object of this invention is a vaccine containing a synthetic or recombinant fragment of the antigen SSP2 which may include all or part of the amino acid sequence shown as Sequence 2 and which causes the production of specific immune sera and immune cells and protects against malaria.

A further object of the invention is a recombinant molecule containing all or part of the DNA and deduced amino acid sequence of SSP2.

These and additional objects of the invention are accomplished by a protein antigen on the surface of Plasmodium sporozoites. The *P. yoelii* SSP2 antigen is detected by a monoclonal antibody (NYS4) which is specific for a 140 kilodalton (kD) protein on the *P. yoelii* sporozoite cell surface. A synthetic peptide containing repeating epitopes of SSP2 derived protein antigen and which is substantially shorter in length than the intact antigen are also part of this invention.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

Figure 1:
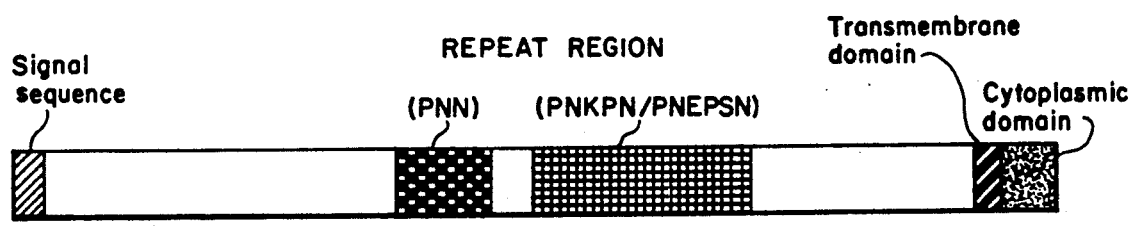
FIG. 1 is a schematic diagram of the predicted general features of the amino acid sequence of P. yoelii SSP2.

Sequences 1 and 2 are the DNA and amino acid sequences, respectively, of this invention.

DESCRIPTION OF THE PREFERRED EMBODIMENTS

A protein antigen (SSP2) on the surface of Plasmodium sporozoites is a candidate immunogen for vaccination against malaria and facilitates research into host immunological responses to malaria. The P. yoelii SSP2 antigen is detected by a monoclonal antibody (NYS4) which is specific for a 140 kilodalton (kD) protein on the sporozoite cell surface. Immunoreactive genomic clones express epitopes of this surface antigen gene and were used to clone the complete gene for P. yoelii SSP2. The DNA sequence of the gene encoding P. yoelii SSP2 and the predicted amino acid sequence (Sequences 1 and 2, respectively) show that it is distinct from the CSP. A synthetic peptide contains repeating epitopes of SSP2 derived protein antigen and is substantially shorter in length than the intact antigen. The peptide, when conjugated to an appropriate carrier molecule, for example keyhole limpet hemocyanin and administered to a host in an appropriate adjuvant, for example Freund's complete adjuvant, elicits antibodies which bind to the SSP2 protein on the sporozoite surface. A recombinant mammalian expression plasmid bearing SSP2 DNA sequences expresses SSP2 epitopes in mammalian cells and the introduction of these transfected cells into mice elicits antibody and cytotoxic T-cell lymphocytic responses which confer partial protection to the recipient animals against challenge infection. In combination, the SSP2 protein and the CS protein elicit immunological responses in the mammalian host which confer 100% protection against challenge infection.

The only previously characterized sporozoite surface antigen, the CSP (Nussenzweig and Nussenzweig, Cell 42:401, 1985), is present on all malaria species studied to date. It is likely that homologs of SSP2 exist in the human malaria species, and that with the current art and the use of the immunological reagents and DNA and protein sequence information disclosed here, they will be identified and used both as vaccine candidates and as reagents for studies of the immune response to malaria and to putative malaria vaccines.

Having described the invention, the following examples are given to illustrate specific applications of the invention including the best mode now known to perform the invention. These specific examples are not intended to limit the scope of the invention described in this application.

EXAMPLE 1

Clones from the Genomic Expression Library

Parasites and DNA isolation. P. yoelii 17X(NL) parasites were obtained by blood passage in Balb/C mice. DNA isolation from parasite infected blood was as described (Wortman et al., Micro. Path., 6:227, 1989). P. yoelii genomic expression libraries were constructed using either 0.5-2.0 or 2.0-7.0 kb fragments generated by partial DNase I digestion, addition of Eco RI linker oligomers, and ligation into the lambda cloning vector gtII by standard techniques. The recombinant phage were packaged in vitro and the resulting library was screened for antigen expressing clones with a 1:20 dilution of a sporozoite surface specific antibody, NYS4, (Charoenvit et al.,*Infect. Immun.*, 55:604, 1989).

EXAMPLE 2

Characterization of SSP2 Antigen

Immuno-fluorescence and Western blotting. Immunofluorescence and Western blotting were carried out as previously described (Charoenvit et al., *Infect. Immun.*, 55:604, 1987). Immunofluoresence showed that NYS4 reacts with a protein on the sporozoite surface. Western blotting showed that protein to have a molecular weight of 140 kD.

Sequence analysis of the 140 kD antigen gene. A clone designated M4 reacted with NYS4. M4 was sequenced and used as a probe to screen the library contaning 2.0-7.0 kb inserts. A clone, designated 10.1111, was found to contain a 4.7 kb insert which overlapped the complete sequence of M4. The DNA sequence of 10.1111 was determined by standard techniques It includes a 2481 bp open reading frame which encodes SSP2. The sequence of 10.1111 and the deduced amino acid sequence of SSP2 is shown in FIG. 1. Like most other malaria antigens, SSP2 contains regions of repeating amino acids. One region consists of a repeating trimer, ProAsnAsn and the other is largely composed of the hexamer, AsnProAsnGluProSer.

EXAMPLE 3

Antibodies to AsnProAsnGluProSer recognize the surface of sporozoites and the 140 kD antigen The overall hydrophilicity of the repeating amino acid sequence AsnProAsnGluProSer suggested it as a potential antigenic determinant (Hopp and Woods, *Proc. Natl. Acad. Sci. USA* 78:3824, 1981). A synthetic peptide containing 3 copies of AsnProAsnGluProSer (18-mer) was strongly recognized by NYS4 in an ELISA and mice immunized with the peptide coupled to keyhole limpet hemocyanin produced antibodies that reacted with sporozoites in an IFAT and with the 140 kD antigen on western blots of sporozoite extracts. These results indicate that the deduced amino acid sequence of SSP2 corresponds to the 140 kD antigen recognized by NYS4 and that the antigenic determinant of NYS4 is contained within the repeating hexamer AsnProAsnGluProSer. It is notable that this repetitive sequence bears no similarity to the major repeats of the P. yoelii CS protein, in which the consensus repeating elements are GlnGlyProGlyAlaPro and GlnGlnProPro (Lal et al., *J. Biol. Chem.*, 262:2937, 1987).

EXAMPLE 4

Cytotoxic lymphocyte responses against SSP2 are protective

We transfected a 1.5 kb fragment of the gene encoding SSP2 into P815 mouse mastocytoma cells. This fragment included amino acids 223 through 698 of Sequence 2 cloned into the mammalian expression vector, pcEXV3 (Miller and Germain, J. Exp. Med. 164:1578, 1986). Nine different clones were derived and each was used to stimulate in vitro spleen cells in culture from BALB/c mice immunized with irradiated P. yoelii sporozoites. SSP2 specific cytotoxic T lymphocytes (CTL) were only present in cultures of spleen cells from immunized mice. All cytotoxic activity was eliminated by in vitro depletion of CD8+T cells, but was unaffected by in vitro depletion of C04+T cells. In BALB/c mice, the protective immunity induced by immunization with irradiated *P. yoelii* sporozoites is eliminated by in vivo treatment of immune mice with antibodies to CD8+T cells, indicating that it is dependent on CTL.

To determine if an immune response directed against SSP2 would provide protection, 8ALB/c mice were injected intraperitoneally 5 times at 2 week intervals with $2 \times 10^8$ irradiated ($10^3$ rads Cesium137) cells of a cloned line of P815 cells transfected with the SSP2 gene linked to pcEXV3. This cloned cell line is designated SSP2 3.9. Two weeks after the last dose, the mice were challenged with 200 *P. yoelii* sporozoites. After immunization with SSP2 3.9 cells, mice produced high levels of antibodies against SSP2 and sporozoites and CTL against SSP2. Four of the six mice were protected against challenge infection by immunization with mastocytoma cells expressing SSP2. Complete protection was demonstrated after immunization with a mixture of two transfected cell lines, SSP2 2.9, and an analogous line consisting of P815 cell transfected with the *P. yoelii* CSP gene and designated CSP 1.5. Furthermore, this regimen induced high levels of antibodies against sporozoites and antigen specific, C08+CTL To determine if this protective immunity, like that found after immunization of BALB/c mice with irradiated sporozoites, was dependent on CD8+T cells, we immunized mice with either SSP2 3.9 or CS 1.5 and then in vivo depleted with anti-CD8 antibody. The partial immunity induced by SSP2, or the CS protein, and the complete protection induced by the combination were completely reversed by depletion of CD8+T cells.

EXAMPLE 5

Identification of the homologs of SSP2 in human malaria species

The protein characteristics, monoclonal antibody, and DNA sequence here disclosed can be used within the current art to detect proteins homologous to SSP2 in the human malaria species *P. falciparum, P. malariae, P. vivax,* and *P. ovale*. For example, oligonucleotide probes based on the DNA sequence or cloned fragments of the SSP2 gene may be used by standard techniques to screen genomic libraries constructed from human malaria species, the cloned gene encoding SSP2 may be expressed in a variety of prokaryotic and eukaryotic expression systems and crude or purified recombinant expressed SSP2 used to produce additional poly or monoclonal antisera or immune T lymphocytes which can be used to screen genomic expression or cDNA libraries in order to identify SSP2 homologs in human malaria species. The original monoclonal antibody NYS4 cannot be used to identify the SSP2 homologs in species other than *P. yoelii*. This is so because NYS4 recognizes an epitope contained within the repeated amino acid sequence AsnProAsnGluProSer. Since the repeated regions of malaria surface antigens are not conserved between species (Weber, Exp. Parasit. 69:303, 1989) it is very unlikely that a monoclonal antibody directed at the repeat sequence of *P. yoelii* SSP2 will recognize SSP2 homologs in other Plasmodium species.

EXAMPLE 6

Use of human malaria homoloqs of SSP2 for vaccination of humans

Given the DNA sequence of the human malaria homologs, readily obtainable with the present art, it is possible to design a large number of vaccine formulations including but not limited to 1) synthetic peptide vaccines based on the inferred amino acid sequence 2) recombinant proteins consisting of all or part of the SSP2 homolog protein expressed in any of a large number of protein expression systems including but not limited to phage lysogens, bacterial plasmids, yeast plasmids, mammalian cell expression plasmids and viruses, and insect viruses (e.g. baculovirus). Vaccines produced by these methods may be administered to humans in any pharmacologically active form and dosage with any pharmacologically appropriate adjuvant including but not limited to saline, aluminum hydroxide, and liposomes. In any of the above vaccines, components derived from the CSP may be included, particulary in light of our finding of the additive effect of immunizing mice with both SSP2 and the CSP.

EXAMPLE 7

Use of transfected cells expressinq SSP2 or its human malaria homologs to study the immune response of humans or animal models to malaria Human or murine cell lines transfected with expression vectors containing the SSP2 gene may be used to study the immune response of humans or experimental animals to naturally acquired or laboratory induced malaria, or to assess the effects of immunization against malaria with irradiated sporozoites or any other putative malaria vaccine. Transfected cells, for example, may serve as target cells in cytotoxicity assays to determine the presence of CTLs directed against SSP2 in humans or animals.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4673 base pairs
        ( B ) TYPE: nucleic acid
        ( C ) STRANDEDNESS: double
        ( D ) TOPOLOGY: linear ( i i ) MOLECULE TYPE: DNA (genomic)

(iii) HYPOTHETICAL: N (iv) ANTI-SENSE: N (vi) ORIGINAL SOURCE:
    (A) ORGANISM: Plasmodium yoelii
    (B) STRAIN: 17X(NL)
    (D) DEVELOPMENTAL STAGE: erythrocytic stage
    (F) TISSUE TYPE: Blood
    (G) CELL TYPE: erythrocytic stage (vii) IMMEDIATE SOURCE:
    (A) LIBRARY: Py-lambdagt11-2-7 kb genomic expression
    (B) CLONE: Py10.1111

(ix) FEATURE:
    (A) NAME/KEY: CDS
    (B) LOCATION: 718..3195
    (D) OTHER INFORMATION:

(xi) SEQUENCE DESCRIPTION: SEQ ID NO:1:

```
CATTAAAACC ATTTAAAAAA GTAAATTTTA TAAATTTTGT TTAATTTTCT TTATATATAT      60

AATATATATA TACATTTATA TATACTCTTG TTCTTTTTAT CGATTAAAAA AATATATAAT     120

ATCCATTATA TTTATTTTTT AACAATTAAA AATATATAAA ATGTACCCCT TGTGCTTGAA     180

GCAACATTTT TTATATTTAA CTGTTGTATC TTTTTTTACA TATATTTGTT CACATTCTTT     240

GGGATGATAT TAAATAATAT AATTTTCGAA GAGAAATATT TTTAAATACT TTTTTTAGTG     300

CTTGCATTAT TTTTATGATA TATATTAACA TTCATAAAAT ATATATTTGT TGAGTGTTGG     360

TTGCCAGTTT ATTGAATTAG CTATATTTTT AAATACTAAA TATATTTTTT TAAATTGGTT     420

ATGATCATAT TCTAATCCGT ATTATATTGC GTATGTGTAT ATATATAACG GAAAAAAAGG     480

AAAACATTTA ATTTCCTCAG ACGCTATTGA ATTAAATTAA CTATATATCA GTTTTATATA     540

AGAAAAGGTA ACACACTCTC TCTCTATATA TATATAATTG CAAACGTGTA GACATTTTTA     600

TATATGGCCA AATAGTAAAT ACAAAATAAT TCCTCACTTT TATTCTCTTA CATATATTAT     660

AATACATACA TAGACACATA ATTTTACCCA TTCCCCATTT CTCTTATAGA CAGAAAC       717
```

| | | | | | | | | | | | | | | | | |
|---|---|---|---|---|---|---|---|---|---|---|---|---|---|---|---|---|
| ATG | AAG | CTC | TTA | GGA | AAT | AGT | AAA | TAT | ATT | TTT | GTT | GTG | CTT | TTA | TTA | 765 |
| Met | Lys | Leu | Leu | Gly | Asn | Ser | Lys | Tyr | Ile | Phe | Val | Val | Leu | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| TGC | ATA | AGC | GTG | TTC | CTT | AAT | GGT | CAG | GAA | ACT | CTT | GAC | GAA | ATA | AAG | 813 |
| Cys | Ile | Ser | Val | Phe | Leu | Asn | Gly | Gln | Glu | Thr | Leu | Asp | Glu | Ile | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| TAT | AGT | GAA | GAA | GTA | TGT | ACC | GAA | CAA | ATC | GAC | ATT | CAT | ATA | TTA | CTA | 861 |
| Tyr | Ser | Glu | Glu | Val | Cys | Thr | Glu | Gln | Ile | Asp | Ile | His | Ile | Leu | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| GAT | GGT | TCA | GGA | AGT | ATT | GGT | TAT | AGC | AAT | TGG | AAG | GCT | CAT | GTT | ATT | 909 |
| Asp | Gly | Ser | Gly | Ser | Ile | Gly | Tyr | Ser | Asn | Trp | Lys | Ala | His | Val | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| CCA | ATG | CTT | AAT | ACT | TTG | GTT | GAT | AAC | TTA | AAT | ATT | TCA | AAT | GAT | GAA | 957 |
| Pro | Met | Leu | Asn | Thr | Leu | Val | Asp | Asn | Leu | Asn | Ile | Ser | Asn | Asp | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ATT | AAT | GTA | TCT | TTG | ACA | CTT | TTT | TCA | ACA | AAT | TCA | CGT | GAA | TTA | ATT | 1005 |
| Ile | Asn | Val | Ser | Leu | Thr | Leu | Phe | Ser | Thr | Asn | Ser | Arg | Glu | Leu | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| AAA | CTT | AAA | GGA | TAT | GGA | TCG | ACT | AGT | AAA | GAC | TCG | CTA | CGT | TTT | ATA | 1053 |
| Lys | Leu | Lys | Gly | Tyr | Gly | Ser | Thr | Ser | Lys | Asp | Ser | Leu | Arg | Phe | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| CTT | GCA | CAT | CTC | CAA | AAT | AAT | TAT | TCA | CCA | AAT | GGT | AAT | ACA | AAT | TTA | 1101 |
| Leu | Ala | His | Leu | Gln | Asn | Asn | Tyr | Ser | Pro | Asn | Gly | Asn | Thr | Asn | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| ACG | AGT | GCA | TTA | TTG | GTT | GTT | GAT | ACT | TTA | ATT | AAT | GAA | AGA | ATG | TAT | 1149 |
| Thr | Ser | Ala | Leu | Leu | Val | Val | Asp | Thr | Leu | Ile | Asn | Glu | Arg | Met | Tyr | |
| | 130 | | | | | 135 | | | | | 140 | | | | | |

-continued

| | | |
|---|---|---|
| CGA CCC GAT GCA ATA CAA TTA GCT ATT ATA TTA ACA GAT GGT ATC CCA<br>Arg Pro Asp Ala Ile Gln Leu Ala Ile Ile Leu Thr Asp Gly Ile Pro<br>145              150               155               160 | 1197 |
| AAT GAT TTA CCT AGA TCT ACT GCG GTT GTG CAT CAA TTA AAA AGA AAA<br>Asn Asp Leu Pro Arg Ser Thr Ala Val Val His Gln Leu Lys Arg Lys<br>               165               170               175 | 1245 |
| CAT GTA AAT GTA GCA ATT ATA GGT GTT GGT GCA GGT GTT AAT AAC GAA<br>His Val Asn Val Ala Ile Ile Gly Val Gly Ala Gly Val Asn Asn Glu<br>        180                   185               190 | 1293 |
| TAT AAT AGA ATT TTA GTT GGA TGT GAT AGA TAC GCA CCA TGC CCA TAC<br>Tyr Asn Arg Ile Leu Val Gly Cys Asp Arg Tyr Ala Pro Cys Pro Tyr<br>     195                 200               205 | 1341 |
| TAC TCT TCT GGT AGT TGG AAT GAA GCC CAA AAT ATG ATA AAA CCT TTT<br>Tyr Ser Ser Gly Ser Trp Asn Glu Ala Gln Asn Met Ile Lys Pro Phe<br>210               215               220 | 1389 |
| CTT ACT AAA GTT TGT CAG GAA GTA GAA AGA ATT GCT CAT TGT GGA AAA<br>Leu Thr Lys Val Cys Gln Glu Val Glu Arg Ile Ala His Cys Gly Lys<br>225               230               235               240 | 1437 |
| TGG GAA GAA TGG AGT GAA TGT TCT ACT ACT TGT GAT GAA GGA AGA AAA<br>Trp Glu Glu Trp Ser Glu Cys Ser Thr Thr Cys Asp Glu Gly Arg Lys<br>               245               250               255 | 1485 |
| ATT AGA AGA AGA CAA ATA TTA CAT CCT GGA TGT GTT AGT GAG ATG ACT<br>Ile Arg Arg Arg Gln Ile Leu His Pro Gly Cys Val Ser Glu Met Thr<br>                   260               265               270 | 1533 |
| ACT CCA TGT AAG GTT CGT GAT TGC CCA CAA ATA CCA ATA CCT CCT GTC<br>Thr Pro Cys Lys Val Arg Asp Cys Pro Gln Ile Pro Ile Pro Pro Val<br>           275               280               285 | 1581 |
| ATC CCT AAT AAA ATT CCA GAA AAG CCA TCA AAC CCA GAA GAA CCA GTA<br>Ile Pro Asn Lys Ile Pro Glu Lys Pro Ser Asn Pro Glu Glu Pro Val<br>290               295               300 | 1629 |
| AAT CCA AAC GAT CCA AAC GAT CCA AAC AAC CCA AAC AAC CCA AAT AAC<br>Asn Pro Asn Asp Pro Asn Asp Pro Asn Asn Pro Asn Asn Pro Asn Asn<br>305               310               315               320 | 1677 |
| CCA AAC AAC CCA AAC AAC CCA AAT AAC CCA AAC AAC CCA AAC AAC CCA<br>Pro Asn Asn Pro Asn Asn Pro Asn Asn Pro Asn Asn Pro Asn Asn Pro<br>               325               330               335 | 1725 |
| AAC AAC CCA AAC AAC CCA AAC AAT CCA AAT AAC CCA AAT AAC CCA AAC<br>Asn Asn Pro Asn Asn Pro Asn Asn Pro Asn Asn Pro Asn Asn Pro Asn<br>                   340               345               350 | 1773 |
| AAC CCA AAT AAC CCA AAT AAC CCA AAC AAC CCA AAT AAC CCA AAC AAC<br>Asn Pro Asn Asn Pro Asn Asn Pro Asn Asn Pro Asn Asn Pro Asn Asn<br>           355               360               365 | 1821 |
| CCA AAT AAC CCA AAT AAC CCA AAT AAC CCA AAT AAC CCA AAC GAT CCA<br>Pro Asn Asn Pro Asn Asn Pro Asn Asn Pro Asn Asn Pro Asn Asp Pro<br>           370               375               380 | 1869 |
| TCA AAC CCA AAC AAC CAC CCA AAA AGG CGA AAC CCA AAA AGG CGA AAC<br>Ser Asn Pro Asn Asn His Pro Lys Arg Arg Asn Pro Lys Arg Arg Asn<br>385               390               395               400 | 1917 |
| CCA AAC AAG CCA AAA CCA AAC AAG CCA AAC CCA AAC AAG CCA AAC CCA<br>Pro Asn Lys Pro Lys Pro Asn Lys Pro Asn Pro Asn Lys Pro Asn Pro<br>               405               410               415 | 1965 |
| AAC GAA CCA TCA AAC CCA AAC AAG CCA AAC CCA AAC GAA CCA TCA AAC<br>Asn Glu Pro Ser Asn Pro Asn Lys Pro Asn Pro Asn Glu Pro Ser Asn<br>                   420               425               430 | 2013 |
| CCA AAC AAG CCA AAC CCA AAC GAA CCA TCA AAC CCA AAC AAG CCA AAC<br>Pro Asn Lys Pro Asn Pro Asn Glu Pro Ser Asn Pro Asn Lys Pro Asn<br>           435               440               445 | 2061 |
| CCA AAT GAG CCA TCA AAC CCA AAC AAG CCA AAC CCA AAT GAG CCA TTA<br>Pro Asn Glu Pro Ser Asn Pro Asn Lys Pro Asn Pro Asn Glu Pro Leu<br>           450               455               460 | 2109 |
| AAC CCA AAC GAG CCA TCA AAT CCA AAC GAG CCA TCA AAC CCA AAT GCG<br>Asn Pro Asn Glu Pro Ser Asn Pro Asn Glu Pro Ser Asn Pro Asn Ala | 2157 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 465 |     |     |     |     | 470 |     |     |     |     | 475 |     |     |     |     | 480 |      |
| CCA | TCA | AAC | CCA | AAC | GAA | CCA | TCA | AAC | CCA | AAT | GAA | CCA | TCA | AAC | CCA | 2205 |
| Pro | Ser | Asn | Pro | Asn | Glu | Pro | Ser | Asn | Pro | Asn | Glu | Pro | Ser | Asn | Pro |      |
|     |     |     |     | 485 |     |     |     |     | 490 |     |     |     |     | 495 |     |      |
| AAT | GAG | CCA | TCA | AAC | CCA | AAC | GAA | CCA | TCA | AAC | CCA | AAT | GAA | CCA | TCA | 2253 |
| Asn | Glu | Pro | Ser | Asn | Pro | Asn | Glu | Pro | Ser | Asn | Pro | Asn | Glu | Pro | Ser |      |
|     |     |     | 500 |     |     |     |     | 505 |     |     |     |     | 510 |     |     |      |
| AAC | CCA | AAA | AAG | CCA | TCA | AAC | CCA | AAT | GAG | CCA | TCA | AAC | CCA | AAT | GAG | 2301 |
| Asn | Pro | Lys | Lys | Pro | Ser | Asn | Pro | Asn | Glu | Pro | Ser | Asn | Pro | Asn | Glu |      |
|     |     | 515 |     |     |     |     | 520 |     |     |     |     | 525 |     |     |     |      |
| CCA | TTA | AAC | CCA | AAT | GAG | CCA | TCA | AAC | CCA | AAC | GAA | CCA | TCA | AAC | CCA | 2349 |
| Pro | Leu | Asn | Pro | Asn | Glu | Pro | Ser | Asn | Pro | Asn | Glu | Pro | Ser | Asn | Pro |      |
|     | 530 |     |     |     |     | 535 |     |     |     |     | 540 |     |     |     |     |      |
| AAC | GAA | CCA | TCA | AAC | CCA | GAA | GAA | CCA | TCA | AAC | CCT | AAA | GAG | CCA | TCA | 2397 |
| Asn | Glu | Pro | Ser | Asn | Pro | Glu | Glu | Pro | Ser | Asn | Pro | Lys | Glu | Pro | Ser |      |
| 545 |     |     |     |     | 550 |     |     |     |     | 555 |     |     |     |     | 560 |      |
| AAC | CCA | AAC | GAA | CCA | TCA | AAC | CCA | GAA | GAG | CCA | AAC | CCA | GAA | GAA | CCA | 2445 |
| Asn | Pro | Asn | Glu | Pro | Ser | Asn | Pro | Glu | Glu | Pro | Asn | Pro | Glu | Glu | Pro |      |
|     |     |     |     | 565 |     |     |     |     | 570 |     |     |     |     | 575 |     |      |
| TCA | AAC | CCT | AAA | GAG | CCA | TCA | AAC | CCA | GAA | GAG | CCA | ATA | AAC | CCA | GAA | 2493 |
| Ser | Asn | Pro | Lys | Glu | Pro | Ser | Asn | Pro | Glu | Glu | Pro | Ile | Asn | Pro | Glu |      |
|     |     |     | 580 |     |     |     |     | 585 |     |     |     |     | 590 |     |     |      |
| GAA | CTA | AAC | CCA | AAA | GAG | CCA | TCA | AAC | CCA | GAA | GAA | TCG | AAC | CCC | AAA | 2541 |
| Glu | Leu | Asn | Pro | Lys | Glu | Pro | Ser | Asn | Pro | Glu | Glu | Ser | Asn | Pro | Lys |      |
|     |     | 595 |     |     |     |     | 600 |     |     |     |     | 605 |     |     |     |      |
| GAG | CCA | ATA | AAC | CCA | GAA | GAA | TCG | AAC | CCC | AAA | GAG | CCA | ATA | AAC | CCA | 2589 |
| Glu | Pro | Ile | Asn | Pro | Glu | Glu | Ser | Asn | Pro | Lys | Glu | Pro | Ile | Asn | Pro |      |
|     | 610 |     |     |     |     | 615 |     |     |     |     | 620 |     |     |     |     |      |
| GAA | GAT | AAT | GAA | AAT | CCA | TTG | ATA | ATA | CAA | GAT | GAA | CCT | ATA | GAA | CCC | 2637 |
| Glu | Asp | Asn | Glu | Asn | Pro | Leu | Ile | Ile | Gln | Asp | Glu | Pro | Ile | Glu | Pro |      |
| 625 |     |     |     |     | 630 |     |     |     |     | 635 |     |     |     |     | 640 |      |
| AGA | AAT | GAT | TCA | AAT | GTA | ATA | CCA | ATT | TTA | CCT | ATC | ATC | CCA | CAA | AAG | 2685 |
| Arg | Asn | Asp | Ser | Asn | Val | Ile | Pro | Ile | Leu | Pro | Ile | Ile | Pro | Gln | Lys |      |
|     |     |     |     | 645 |     |     |     |     | 650 |     |     |     |     | 655 |     |      |
| GGT | AAT | AAT | ATC | CCA | AGC | AAT | CTA | CCA | GAA | AAT | CCA | TCT | GAC | TCA | GAA | 2733 |
| Gly | Asn | Asn | Ile | Pro | Ser | Asn | Leu | Pro | Glu | Asn | Pro | Ser | Asp | Ser | Glu |      |
|     |     |     | 660 |     |     |     |     | 665 |     |     |     |     | 670 |     |     |      |
| GTA | GAA | TAT | CCA | AGA | CCA | AAT | GAT | AAT | GGT | GAA | AAT | TCA | AAT | AAT | ACT | 2781 |
| Val | Glu | Tyr | Pro | Arg | Pro | Asn | Asp | Asn | Gly | Glu | Asn | Ser | Asn | Asn | Thr |      |
|     |     | 675 |     |     |     |     | 680 |     |     |     |     | 685 |     |     |     |      |
| ATG | AAA | TCA | AAA | AAA | AAT | ATA | CCC | AAC | GAG | CCT | ATA | CCA | TCA | CCA | GGT | 2829 |
| Met | Lys | Ser | Lys | Lys | Asn | Ile | Pro | Asn | Glu | Pro | Ile | Pro | Ser | Pro | Gly |      |
|     | 690 |     |     |     |     | 695 |     |     |     |     | 700 |     |     |     |     |      |
| GAT | AAC | CCA | TAT | AAA | GGT | CAC | GAA | GAA | AGA | ATA | CCA | AAA | CCT | CAT | CGA | 2877 |
| Asp | Asn | Pro | Tyr | Lys | Gly | His | Glu | Glu | Arg | Ile | Pro | Lys | Pro | His | Arg |      |
| 705 |     |     |     |     | 710 |     |     |     |     | 715 |     |     |     |     | 720 |      |
| TCA | AAT | GAT | GAC | TAT | GTA | TAT | GAT | AAT | AAT | GTA | AAT | AAA | AAT | AAT | AAA | 2925 |
| Ser | Asn | Asp | Asp | Tyr | Val | Tyr | Asp | Asn | Asn | Val | Asn | Lys | Asn | Asn | Lys |      |
|     |     |     |     | 725 |     |     |     |     | 730 |     |     |     |     | 735 |     |      |
| GAT | GAA | CCA | GAA | ATT | CCA | AAT | AAT | GAG | TAT | GAA | GAG | GAT | AAA | AAT | AAA | 2973 |
| Asp | Glu | Pro | Glu | Ile | Pro | Asn | Asn | Glu | Tyr | Glu | Glu | Asp | Lys | Asn | Lys |      |
|     |     |     | 740 |     |     |     |     | 745 |     |     |     |     | 750 |     |     |      |
| AAC | CAG | TCT | AAA | TCT | AAT | AAT | GGA | TAT | AAA | ATT | GCT | GGT | GGT | ATT | ATT | 3021 |
| Asn | Gln | Ser | Lys | Ser | Asn | Asn | Gly | Tyr | Lys | Ile | Ala | Gly | Gly | Ile | Ile |      |
|     |     | 755 |     |     |     |     | 760 |     |     |     |     | 765 |     |     |     |      |
| GGA | GGA | TTA | GCT | ATA | CTT | GGA | TGT | GCA | GGT | GTT | GGT | TAT | AAT | TTT | ATA | 3069 |
| Gly | Gly | Leu | Ala | Ile | Leu | Gly | Cys | Ala | Gly | Val | Gly | Tyr | Asn | Phe | Ile |      |
|     | 770 |     |     |     |     | 775 |     |     |     |     | 780 |     |     |     |     |      |
| GCA | GGA | AGT | AGC | GCT | GCA | GGA | TTG | GCT | GGA | GCA | GAG | CCT | GCA | CCT | TTT | 3117 |
| Ala | Gly | Ser | Ser | Ala | Ala | Gly | Leu | Ala | Gly | Ala | Glu | Pro | Ala | Pro | Phe |      |
| 785 |     |     |     |     | 790 |     |     |     |     | 795 |     |     |     |     | 800 |      |

-continued

| | | | | | | | | | | | | | | | |
|---|---|---|---|---|---|---|---|---|---|---|---|---|---|---|---|
| GAA | GAT | GTA | ATT | CCA | GAT | GAT | GAC | AAA | GAT | ATT | GTT | GAA | AAC | GAA | CAG | 3165
| Glu | Asp | Val | Ile | Pro | Asp | Asp | Asp | Lys | Asp | Ile | Val | Glu | Asn | Glu | Gln |
| | | | | 805 | | | | 810 | | | | | 815 | | |

| | | | | | | | | | |
|---|---|---|---|---|---|---|---|---|---|
| TTT | AAA | TTA | CCT | GAA | GAT | AAT | GAC | TGG | AAC | TAATTTTAAT AAACGTATAT | 3215
| Phe | Lys | Leu | Pro | Glu | Asp | Asn | Asp | Trp | Asn |
| | | | 820 | | | | | 825 | |

```
ATCCACTTTA TTATTCTTAT ATTACATACA AATCTGATAT ATGTTTGTCT TTTTTTTGCT    3275
TTTAAATATT ATCTATGATT ATATATATAA TATACCTTTA AATAATAAAT TCATAAATTC    3335
GCTTGTCTTT AAATTGTTTG TGTTTCTTTA CACTTTATTC CTTTTCCTG TTTTTGTTCC     3395
TTTTTTTTTG TATGATTAAG TTATTTAAA TTAACAGTTT GATAAATTGT CATCTTTTA      3455
TGTTATTCAT TCAATTATAT ATCCATTTAT TTTCATATTT TTTTTAACG ATTTTTTTT      3515
AACTATTTTT TTTTAACTAA TTGTCTCGTT ATAATATATA TATTTATTTA TACTCCAATA    3575
TTTAATGGTT ACAATTATTC TTAATATAAA AAAAAAAAAA AAAAAAAAA ACTTAAAAGT     3635
TAATAACATT TTTAGGTTTG TATATTTACA CGGTATTTAC TATTTTCAAA ATAATTATGA    3695
ATAAAACAAA AAAGTGATAA TACATAATAA AATGAATTCC TAAAAAAATA GACAAATCCA    3755
CCAATATTAT CGATAAAAAA GAAATAAACA AAATGTGATT ATTTTAAAAT TTACAAAACA    3815
TAAAAATAAT GGTCTTAAGT TTTATGAACT AAAAAGTGTG ATAAAAAAAA ATGATGGAAT    3875
GTTAAAAAAG AGAATATCTA AAGTTGGCTC ATGATTTTTT GAAGTATTAT CATCCTTATT    3935
ATACATATCT GAAATTTTTA ATTTTTCATA TAAACTTTTC GAAAATTCAT AATTTTGTAT    3995
TTTCATATCT GTGTTATTAT GTTTGGATTC ATTTATTATA TTATTTGTGT AAAAATTAAG    4055
ATGATATATT TTTAGCATAT TTGACAAATT GTCAAATTCG TTGTATTCTG TTTTTGAAAA    4115
AATATGAGCA TTTTTTTTAA TATTATTATT CTCTTTCATT TTACAAAAAA ATAAGAATCG    4175
ATTTTTTTT TTTAAATCAT TAAAATTAAT TTTATTTTA AGAGAAGCAA TATCATTTTC      4235
CAATTTATTT TCATTTTCTT CATTATTTGT AGTTGCATGT GTCCATTTTT TGTTTGGAGC    4295
ATATAAATTT ATTAATTCTT TATTGCTTAA TTCTTTATTT TGTAAATTTA TTAATTTTGA    4355
GTATTGTATA TATATTTCAT CCATTTTGT CTTGTTCATA TTATTAGGAA AGGAAATAAT     4415
ATTCTTATTT GTATCAATAC ATTTATTTTT ATTTTTCCTT TTATAAAAAA TCGAATAAAA    4475
TTCTAATAAC GCCATTACCT CTACCTTTTC ATAATTTGAA GTATCATATA ATGTGAATAA    4535
ATTTATAATG TTCCCTTCTA GTTCGTTTAT TTTACATATT TCTTTTCCAT ATTGTATATT    4595
ACCAATCATG TTTTCGTTTG TTCTTTATTT ATCTTATATC CCATTTTACT TATAGCTCGT    4655
GTTTCCTCCA TTTTCTGG                                                   4673
```

( 2 ) INFORMATION FOR SEQ ID NO:2:

( i ) SEQUENCE CHARACTERISTICS:
      ( A ) LENGTH: 826 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Leu | Leu | Gly | Asn | Ser | Lys | Tyr | Ile | Phe | Val | Val | Leu | Leu | Leu |
| 1 | | | | 5 | | | | 10 | | | | | 15 | | |

| | | | | | | | | | | | | |
|---|---|---|---|---|---|---|---|---|---|---|---|---|
| Cys | Ile | Ser | Val | Phe | Leu | Asn | Gly | Gln | Glu | Thr | Leu | Asp | Glu | Ile | Lys |
| | | | 20 | | | | | 25 | | | | | 30 | | |

| | | | | | | | | | | | | |
|---|---|---|---|---|---|---|---|---|---|---|---|---|
| Tyr | Ser | Glu | Glu | Val | Cys | Thr | Glu | Gln | Ile | Asp | Ile | His | Ile | Leu | Leu |
| | | 35 | | | | | 40 | | | | | 45 | | | |

| | | | | | | | | | | | | |
|---|---|---|---|---|---|---|---|---|---|---|---|---|
| Asp | Gly | Ser | Gly | Ser | Ile | Gly | Tyr | Ser | Asn | Trp | Lys | Ala | His | Val | Ile |
| | 50 | | | | | 55 | | | | | 60 | | | | |

```
Pro Met Leu Asn Thr Leu Val Asp Asn Leu Asn Ile Ser Asn Asp Glu
65                  70                  75                  80

Ile Asn Val Ser Leu Thr Leu Phe Ser Thr Asn Ser Arg Glu Leu Ile
                85                  90                  95

Lys Leu Lys Gly Tyr Gly Ser Thr Ser Lys Asp Ser Leu Arg Phe Ile
            100                 105                 110

Leu Ala His Leu Gln Asn Asn Tyr Ser Pro Asn Gly Asn Thr Asn Leu
            115                 120                 125

Thr Ser Ala Leu Leu Val Val Asp Thr Leu Ile Asn Glu Arg Met Tyr
130                     135                 140

Arg Pro Asp Ala Ile Gln Leu Ala Ile Ile Leu Thr Asp Gly Ile Pro
145                 150                 155                 160

Asn Asp Leu Pro Arg Ser Thr Ala Val Val His Gln Leu Lys Arg Lys
                165                 170                 175

His Val Asn Val Ala Ile Ile Gly Val Gly Ala Gly Val Asn Asn Glu
            180                 185                 190

Tyr Asn Arg Ile Leu Val Gly Cys Asp Arg Tyr Ala Pro Cys Pro Tyr
            195                 200                 205

Tyr Ser Ser Gly Ser Trp Asn Glu Ala Gln Asn Met Ile Lys Pro Phe
210                 215                 220

Leu Thr Lys Val Cys Gln Glu Val Glu Arg Ile Ala His Cys Gly Lys
225                 230                 235                 240

Trp Glu Glu Trp Ser Glu Cys Ser Thr Thr Cys Asp Glu Gly Arg Lys
                245                 250                 255

Ile Arg Arg Arg Gln Ile Leu His Pro Gly Cys Val Ser Glu Met Thr
            260                 265                 270

Thr Pro Cys Lys Val Arg Asp Cys Pro Gln Ile Pro Ile Pro Pro Val
        275                 280                 285

Ile Pro Asn Lys Ile Pro Glu Lys Pro Ser Asn Pro Glu Glu Pro Val
290                 295                 300

Asn Pro Asn Asp Pro Asn Asp Pro Asn Asn Pro Asn Asn Pro Asn Asn
305                 310                 315                 320

Pro Asn Asn Pro Asn Asn Pro Asn Asn Pro Asn Asn Pro Asn Asn Pro
                325                 330                 335

Asn Asn Pro Asn Asn Pro Asn Asn Pro Asn Asn Pro Asn Asn Pro Asn
            340                 345                 350

Asn Pro Asn Asn Pro Asn Asn Pro Asn Asn Pro Asn Asn Pro Asn Asn
        355                 360                 365

Pro Asn Asn Pro Asn Asn Pro Asn Asn Pro Asn Asn Pro Asn Asp Pro
        370                 375                 380

Ser Asn Pro Asn Asn His Pro Lys Arg Arg Asn Pro Lys Arg Arg Asn
385                 390                 395                 400

Pro Asn Lys Pro Lys Pro Asn Lys Pro Asn Pro Asn Lys Pro Asn Pro
                405                 410                 415

Asn Glu Pro Ser Asn Pro Asn Lys Pro Asn Pro Asn Glu Pro Ser Asn
                420                 425                 430

Pro Asn Lys Pro Asn Pro Asn Glu Pro Ser Asn Pro Asn Lys Pro Asn
            435                 440                 445

Pro Asn Glu Pro Ser Asn Pro Asn Lys Pro Asn Pro Asn Glu Pro Leu
            450                 455                 460

Asn Pro Asn Glu Pro Ser Asn Pro Asn Glu Pro Ser Pro Asn Ala
465                 470                 475                 480

Pro Ser Asn Pro Asn Glu Pro Ser Asn Pro Asn Glu Pro Ser Asn Pro
                485                 490                 495

Asn Glu Pro Ser Asn Pro Asn Glu Pro Ser Asn Pro Asn Glu Pro Ser
```

-continued

```
                          500                         505                          510
Asn  Pro  Lys  Lys  Pro  Ser  Asn  Pro  Asn  Glu  Pro  Ser  Asn  Pro  Asn  Glu
          515                      520                     525
Pro  Leu  Asn  Pro  Asn  Glu  Pro  Ser  Asn  Pro  Asn  Glu  Pro  Ser  Asn  Pro
     530                           535                     540
Asn  Glu  Pro  Ser  Asn  Pro  Glu  Glu  Pro  Ser  Asn  Pro  Lys  Glu  Pro  Ser
545                      550                      555                           560
Asn  Pro  Asn  Glu  Pro  Ser  Asn  Pro  Glu  Glu  Pro  Asn  Pro  Glu  Glu  Pro
               565                           570                          575
Ser  Asn  Pro  Lys  Glu  Pro  Ser  Asn  Pro  Glu  Glu  Pro  Ile  Asn  Pro  Glu
               580                           585                     590
Glu  Leu  Asn  Pro  Lys  Glu  Pro  Ser  Asn  Pro  Glu  Glu  Ser  Asn  Pro  Lys
          595                      600                          605
Glu  Pro  Ile  Asn  Pro  Glu  Glu  Ser  Asn  Pro  Lys  Glu  Pro  Ile  Asn  Pro
     610                      615                      620
Glu  Asp  Asn  Glu  Asn  Pro  Leu  Ile  Ile  Gln  Asp  Glu  Pro  Ile  Glu  Pro
625                           630                     635                      640
Arg  Asn  Asp  Ser  Asn  Val  Ile  Pro  Ile  Leu  Pro  Ile  Ile  Pro  Gln  Lys
                    645                      650                          655
Gly  Asn  Asn  Ile  Pro  Ser  Asn  Leu  Pro  Glu  Asn  Pro  Ser  Asp  Ser  Glu
               660                      665                          670
Val  Glu  Tyr  Pro  Arg  Pro  Asn  Asp  Asn  Gly  Glu  Asn  Ser  Asn  Asn  Thr
          675                      680                     685
Met  Lys  Ser  Lys  Lys  Asn  Ile  Pro  Asn  Glu  Pro  Ile  Pro  Ser  Pro  Gly
     690                           695                     700
Asp  Asn  Pro  Tyr  Lys  Gly  His  Glu  Glu  Arg  Ile  Pro  Lys  Pro  His  Arg
705                      710                      715                          720
Ser  Asn  Asp  Asp  Tyr  Val  Tyr  Asp  Asn  Asn  Val  Asn  Lys  Asn  Asn  Lys
                    725                      730                          735
Asp  Glu  Pro  Glu  Ile  Pro  Asn  Asn  Glu  Tyr  Glu  Glu  Asp  Lys  Asn  Lys
               740                      745                     750
Asn  Gln  Ser  Lys  Ser  Asn  Asn  Gly  Tyr  Lys  Ile  Ala  Gly  Gly  Ile  Ile
          755                      760                     765
Gly  Gly  Leu  Ala  Ile  Leu  Gly  Cys  Ala  Gly  Val  Gly  Tyr  Asn  Phe  Ile
     770                      775                     780
Ala  Gly  Ser  Ser  Ala  Ala  Gly  Leu  Ala  Gly  Ala  Glu  Pro  Ala  Pro  Phe
785                      790                      795                          800
Glu  Asp  Val  Ile  Pro  Asp  Asp  Asp  Lys  Asp  Ile  Val  Glu  Asn  Glu  Gln
               805                      810                          815
Phe  Lys  Leu  Pro  Glu  Asp  Asn  Asp  Trp  Asn
               820                 825
```

Obviously, many modifications and variations of the present invention are possible in light of the above teachings. It is therefore to be understood that, within the scope of the appended claims, the invention may be practiced otherwise than as specifically described.

What we claim is:

1. A protein selected from the group consisting of recombinant and synthetic protein having the amino acid sequence shown in Sequence ID No. 2, fragments of that protein and homologs of that protein in other Plasmodium species selected from the group consisting of *Plasmodium yoelii, Plasmodium falciparum, Plasmodium vivax, Plasmodium malariae,* and *Plasmodium ovale.*

2. The protein of claim 1 wherein the fragment consists of amino acids 223 through 698 of Sequence 2 and homologs of that fragment in other Plasmodium species.

* * * * *